United States Patent
Shalaby

(10) Patent No.: US 7,722,914 B2
(45) Date of Patent: May 25, 2010

(54) MICROMANTLED DRUG-ELUTING STENT

(75) Inventor: Shalaby W. Shalaby, Anderson, SC (US)

(73) Assignee: Poly-Med, Inc, Anderson, SC (US)

( * ) Notice: Subject to any disclaimer, the term of this patent is extended or adjusted under 35 U.S.C. 154(b) by 0 days.

(21) Appl. No.: 12/152,390

(22) Filed: May 14, 2008

(65) Prior Publication Data

US 2008/0241352 A1 Oct. 2, 2008

Related U.S. Application Data

(60) Division of application No. 11/390,403, filed on Mar. 27, 2006, now Pat. No. 7,416,559, which is a continuation-in-part of application No. 10/630,320, filed on Jul. 30, 2003, now Pat. No. 7,070,858, which is a division of application No. 10/003,640, filed on Nov. 2, 2001, now abandoned, which is a continuation-in-part of application No. 09/698,527, filed on Oct. 27, 2000, now Pat. No. 6,462,169.

(51) Int. Cl.
   B05D 3/14 (2006.01)
   A61F 2/06 (2006.01)
   B05C 5/04 (2006.01)

(52) U.S. Cl. .............. 427/2.1; 427/2.24; 427/2.25; 623/1.1; 623/1.15; 623/1.2; 623/1.42; 623/1.54; 118/621

(58) Field of Classification Search ............ 427/2.1, 427/2.24; 623/1.1, 1.15, 1.42, 1.44, 1.46, 623/23.7

See application file for complete search history.

(56) References Cited

U.S. PATENT DOCUMENTS

| | | | |
|---|---|---|---|
| 4,429,080 A | 1/1984 | Casey | |
| 4,470,416 A | 9/1984 | Kafrawy | |
| 4,532,928 A | 8/1985 | Bezwada | |
| 4,543,952 A | 10/1985 | Shalaby | |
| 5,133,739 A | 7/1992 | Bezwada | |
| 5,403,347 A | 4/1995 | Roby | |
| 5,431,679 A | 7/1995 | Bennett | |
| 5,468,253 A | 11/1995 | Bezwada | |
| 5,554,170 A | 9/1996 | Roby | |
| 5,620,461 A | 4/1997 | Muijs Van de Moer | |
| 5,644,002 A | 7/1997 | Cooper | |
| 5,713,920 A | 2/1998 | Bezwada | |
| 5,849,415 A * | 12/1998 | Shalaby et al. | 428/419 |
| 5,951,997 A | 9/1999 | Bezwada | |
| 6,206,908 B1 | 3/2001 | Roby | |
| 6,462,169 B1 | 10/2002 | Shalaby | |
| 6,794,485 B2 | 9/2004 | Shalaby | |
| 6,797,485 B2 | 9/2004 | Cassels | |
| 7,070,858 B2 | 7/2006 | Shalaby | |
| 2003/0211135 A1 * | 11/2003 | Greenhalgh et al. | 424/443 |
| 2003/0215624 A1 * | 11/2003 | Layman et al. | 428/221 |
| 2004/0030377 A1 * | 2/2004 | Dubson et al. | 623/1.13 |
| 2007/0043428 A1 * | 2/2007 | Jennings et al. | 623/1.15 |
| 2008/0027531 A1 * | 1/2008 | Reneker et al. | 623/1.15 |

FOREIGN PATENT DOCUMENTS

| | | |
|---|---|---|
| EP | 0 618 250 A1 | 10/1994 |
| EP | 0 697 427 A2 | 2/1996 |
| EP | 0 712 880 A2 | 5/1996 |
| EP | 0 737 703 A2 | 10/1996 |

OTHER PUBLICATIONS

Correa et al., Sixth World Biomaterials Congress, Trans So.c Biomat., II, 992 (2000).
L. Mandelkern, Crystallization of Polymers, McGraw-Hill Book Company, NY, 1964, p. 105-106.
S.W. Shalaby, Chapter 3 of Thermal Characterization of Polymeric Materials (E.A. Turi ed.) Academic Press, NY, 1981, p. 330.
S.W. Shalaby and H.E. Blair, Chapter 4 of Thermal Characterization of Polymeric Materials (E.A. Turi ed.) Academic Press, NY, 1981, p. 402.

* cited by examiner

*Primary Examiner*—Timothy H Meeks
*Assistant Examiner*—Cachet I Sellman
(74) *Attorney, Agent, or Firm*—Leigh P Gregory

(57) ABSTRACT

Pharmacologically active, easy-to-deploy, biomechanically compatible, inflatable endovascular, drug-eluting stent are formed of a primary expandable polymeric or metallic construct, intimately mantled with a biomechanically compatible, polymeric microporous, microfibrous, compliant, stretchable fabric formed by direct electrospinning onto the outside surface of the primary construct using at least one polymer solution containing at least one active compound, selected from those expected to control key biological events leading to in-stent restenosis.

2 Claims, No Drawings

MICROMANTLED DRUG-ELUTING STENT

The present is a divisional application of U.S. Ser. No. 11/390,403, filed Mar. 27, 2006 now U.S. Pat. No. 7,416,559, which is a continuation-in-part of U.S. Ser. No. 10/630,320, filed Jul. 30, 2003, now issued as U.S. Pat. No. 7,070,858, which was a divisional application of U.S. Ser. No. 10/003,640, filed Nov. 2, 2001, now abandoned, which was a continuation-in-part of U.S. Ser. No. 09/698,527, filed Oct. 27, 2000, now issued as U.S. Pat. No. 6,462,169.

FIELD OF THE INVENTION

This invention is directed toward a three-component bioactive device that is designed to fulfill the unmet requirements to minimize or preferably, eliminate restenosis associated with endovascular stents. The subject bioactive device is a micromantled drug-eluting stent comprising a rigid, porous primary stent construct, which can be metallic or polymeric, mantled with a biomechanically compatible, polymeric, microporous, microfibrous, compliant, stretchable fabric formed by direct electrostatic spinning on the outside surface of said primary construct using a least one polymer solution containing at least one active compound in each individual solution. The active compounds are selected primarily for their antiproliferative, immunosuppressive, and anti-inflammatory activities, among other properties, which prevent, in part, smooth muscle cells proliferation and promoting endothelial cell growth.

BACKGROUND OF THE INVENTION

Coronary artery bypass grafting was to be the surgical solution to coronary atherosclerosis. When percutaneous transluminal coronary angioplasty was introduced, it seemed to be the less-invasive alternative to coronary artery bypass grafting. Percutaneous transluminal coronary angioplasty with stenting then evolved to solve the issue of post-percutaneous transluminal coronary angioplasty artery collapse. The stents which have been used and are still being used in these procedures are small wire-mesh tubes that are commonly made of stainless steel or Nitinol. These devices are tightly secured on a balloon catheter and are gently guided to an area of occlusion within the coronary arteries. Once properly placed, the balloon is pressurized, resulting in the expansion of the stent and diseased blood vessel wall. The balloon catheter is then retracted, and the stent remains in place, providing mechanical support to keep the blood vessel open for increased blood flow to the heart. Various metal stents have been shown to reduce the restenosis rate compared with angioplasty alone. However, as in most fast-developing technology, percutaneous transluminal coronary angioplasty with stenting did not fully prevent the clinically challenging phenomenon of restenosis. This entails the narrowing of the stented coronary artery attributed to excessive smooth muscle cell proliferation (scarring) beneath the vessel's endothelium. Restenosis, which occurs in 25-30 percent of stented patients, is of no small concern to cardiology interventionists as well as to patients who have stents in situ or who are candidates for a stenting procedure. Among the factors contributing to restenosis is the biomechanical incompatibility of the high modulus of the metallic stent material and frequently acute geometries of their components contacting the soft luminal surface leading to complex traumatic events, including inflammation of cell lining of such surface. The biomechanical incompatibility was among the factors that prompted the pursuit of the study subject of the present invention, where a compliant polymer mantle is present between the high modulus stent construct and the soft luminal surface. For the past few years, the combination technology of devices in the form of stents and drugs capable of controlling one or more of the biological events contributing to restenosis led to the development of drug-eluting stents. These are, so far, based on metallic stent constructs with drug-bearing coatings. In effect, the drug-eluting stents were developed to eliminate (or at least diminish) the occurrence of restenosis in the coronary arteries after stenting. In very simple terms, a drug-eluting stent is one that is overcoated with a pharmaceutical agent that prevents or reduces the undesirable smooth muscle cell proliferation that occurs at the stent-delivery site, and thereby impedes recurrent stenosis. Recently, the drug-eluting stents have been introduced into clinical use. These stents were shown to reduce significantly the build up of tissue (in-stent restenosis) that occurs after the injurious effect of stent delivery. Commonly, metal stents are coated with a thin, usually nonabsorbable polymer that serves as the drug reservoir. In this way, a small amount of a highly potent drug can be delivered over a short period, usually 30 days. After the drug elutes from the thin polymer coating, the metal stent and the residual polymer coating remain in place. Over time, the permanent presence of the nonabsorbable device may lead to complications at the implant site.

Toward improving the biomechanical compatibility of the stents, while releasing a pharmaceutical agent, which can by themselves impede recurrent stenosis, a number of investigators of the prior art developed several forms of drug-containing absorbable and non-absorbable polymeric stents made of relatively lower modulus materials compared to metals. The rationale for nondegradable stents was the improved biocompatibility over the metal stent and convenient drug loading. Nonabsorbable polymers being investigated for stent use include polyethylene terephthalate, polyurethane, and polydimethyl siloxane. However, apart from the biomechanical compatibility, the nonabsorbable stents were inferior to their metallic counterparts in terms of their ease of deployment and retention of their physicomechanical properties at vascular sites. Meanwhile, the rationale for absorbable stents was support of body conduits only during their healing, delivery of drug from an internal reservoir to the surrounding tissue, without the need for surgery to remove the device. The most frequently used polymers for bioabsorbable stents are aliphatic polyesters, such as poly(L-lactic acid) (PLLA), poly(glycolic acid) (PGA), and poly($\epsilon$-caprolactone) (PCL). Nonetheless, most of the stents described in the prior art are made of PLLA. An interesting design of the PLLA stent required expansion with a heated balloon, which represented an additional risk to the patient. Accordingly, this stent has not been commercialized. Another disadvantage of stents made of PLLA and similar polymers is their lack of visibility by X-ray radiography/fluoroscopy. This is a critical disadvantage as the physician relies on X-ray images to guide the stent to the location of the diseased vessel, as well as monitoring the performance of the stent after implantation. This disadvantage has contributed to the limited clinical and commercial acceptance of absorbable polymer stents.

It is well accepted that in-stent restenosis, the major adverse outcome after percutaneous coronary stent placement, can be successfully reduced by drug-eluting stents releasing cytostatic compounds. Numerous large clinical trials consistently revealed an impressive reduction of in-stent restenosis in de novo lesions by drug-eluting stents. However, in specific patient subsets, such as insulin-dependent diabetic subjects, or in challenging interventional scenarios, like bifurcation stenting, the rate of restenosis remains to be substantial at this point. Moreover, the outcome of treatment of in-stent restenosis with drug-eluting stents is currently not satisfactorily solved. Dose adjustments at the discretion of the interventional cardiologist to individualize the dosage of the compound on the drug-eluting stent may be desirable to enable an individual dose adjustment for specific lesion or patient subsets, e.g., higher rapamycin doses for diabetic patients. This provided a strong incentive to pursue a key segment of this invention where multiple bioactive agents are allowed to elute under controlled conditions, for instance, to inhibit smooth muscle cell proliferation and promote re-endothelialization.

Following the evolution of endovascular stent technology as noted above, it is obvious that (1) metallic stents suffer primarily from biomechanical compatibility as it relates to injuries to the vascular luminal wall; (2) coating the metallic stent with drug-bearing thin polymer film does reduce, to a limited extent, the effect of the biomechanical incompatibility of the stent—the coating does not totally eliminate the undesirable physical effect of the high modulus metal in contact with the vascular luminal wall; (3) the drug-eluting stents do not provide a precise control of the drug in concert with different prevailing critical biological events—this may be related, in part, to coating non-uniformity; and (4) use of absorbable stents as low modulus alternatives to metallic stents suffer primarily from their far-from-optimal ability to be deployed, inflated, and retain mechanical integrity at the application site compared to their metallic counterparts.

In an earlier disclosure by the present inventor (U.S. Pat. No. 6,797,485), a highly compliant, expandable, tubular mantle sleeve or cover made of absorbable, highly compliant polyaxial copolyester was described to be placed tightly outside an expandable metallic or polymeric stent so that under concentric irreversible expansion at the desired site of a treated biological conduit, such as blood vessel or an urethra, both components will simultaneously expand and the mantle provides a barrier between the inner wall of the conduit and the outer wall of the stent. In another aspect of that disclosure, the subject copolymers are used as a stretchable matrix of a fiber-reinforced cover sleeve, or mantle for a stent, wherein the fiber reinforcement is in the form of spirally coiled yarn (with and without crimping) woven, knitted, or braided construct. In effect, U.S. Pat. No. 6,797,485, describes a composite tubular cover or mantle for a stent, wherein the latter comprises a polymeric matrix reinforced with monofilament cross-spiral, wherein at least one of the matrix and reinforcement comprise an absorbable crystalline, monocentric, polyaxial copolyester and wherein the composite tubular cover or mantle can be microporous. However, both the tubular mantle and composite tubular mantle (1) are made independent of the stent and then placed in said stent; (2) are produced, in part, by casting a polymer solution on the mandrill (not the stent) and then allowed to dry; (3) are made to have much higher bulk density as compared to the electrospun mantle subject of this invention, which provides considerably higher compressibility and engineering compliance—this makes the electrospun mantle a more effective shock absorber between the high modulus metallic stent and the soft luminal wall, as compared to the mantle of U.S. Pat. No. 6,797,485 with its relatively high bulk density; and (4) have a much lower surface/volume ratio and practically one type of matrix that provides one diffusion pathway for drug elution as compared to the electrospun mantle of the present invention, which provides more than one type of matrices with high surface/volume ratio which makes it more suitable for more uniform and precise control of more than one drug at more than one diffusion rate and pathway.

SUMMARY OF THE INVENTION

Analysis of the events associated with the evolution of the stent technology provided the basis for conceiving the different segments of the present invention, which (1) emphasize the need for a high modulus, porous primary construct made of metallic or polymeric materials with metal-like deformability to avoid complications with stent deployment and retention of physical properties at the application site; (2) the use of an absorbable or non-absorbable, compliant microfibrous mantle on the primary construct to act as a soft pad between components of the high modulus, primary construct so as to eliminate the direct effect of its high modulus; and (3) provide a polymeric matrix comprising microfibrous fabric that permits the use of more than one drug release in a precise, controlled manner that can be achieved with non-uniform or even uniform coating.

Accordingly, the present invention is directed to a micromantled, drug-eluting endovascular stent which is a high modulus, expandable, porous scaffold onto which is directly electrostatically spun, a stretchable, compliant, microfibrous, non-woven mantle having at least one type of bioactive agent, wherein the scaffold is metallic and the mantle is an electrostatically spun fabric of at least one type of polymeric microfiber, and wherein the mantle includes at least one type of bioactive agent selected from antimicrobials, antineoplastic agents, immunosuppressants, non-steroidal anti-inflammatory drugs, antibiotics, anti-arthritic agents, smooth muscle cell growth inhibitors, anti-proliferative agents, anti-infective agents and endothelial cell growth promoters, such as a vascular endothelial growth factor (VEGF) or a polypeptide functional analog.

A specific aspect of this invention is directed to a micromantled, drug-eluting endovascular stent which is a high modulus, expandable, porous scaffold onto which is electrostatically spun, a stretchable, compliant, microfibrous, non-woven mantle having at least one type of bioactive agent, wherein the mantle includes at least one bioactive agent selected from leflunamide, clotrimazole, thalidomide, methotrexate, indomethacin, dexamethasone, D-penicillamine, mycophenolate mofetil, dihydrofolate reductase, deferoxamine, paclitaxel, curcumin, rapamycin, trimetrexate glucuronate, naproxen, mitomycin, mitoxantrone, and topotecan, and wherein the microfibrous mantle is formed of electrostatically spun microfibers made of at least from one copolymer selected from absorbable polyaxial copolyesters, polyether-copolyester block copolymers, absorbable C-succinylated polyaxial copolyesters, absorbable C-succinylated polyether-copolyester block copolymers, non-absorbable copolymers derived from at least one alkyl methacrylate and maleic anhydride, non-absorbable copolymers derived from at least one alkyl methacrylate and methacrylic acid, and non-absorbable copolymers derived from at least one alkyl methacrylate and N-vinyl pyrrolidone.

Another specific aspect of this invention is directed to a micromantled, drug-eluting endovascular stent which is a high modulus, expandable, porous scaffold onto which is electrostatically spun, a stretchable, compliant, microfibrous, non-woven mantle having at least one type of bioactive agent, wherein the microfibrous mantle includes at least two types of electrostatically spun fibers containing dissimilar bioactive agents, wherein each of the two types of fibers elute at differing rates. Specifically, one type of the electrospun microfibers represents a relatively fast-eluting matrix of a bioactive agent or agents while a second type of electrospun fibers represents a relatively slow-eluting matrix of a bioactive agent or agents. Preferably, the relatively fast-eluting microfibers contain at least one bioactive agent selected from non-steroidal anti-inflammatory drugs, immunosuppressants, anti-arthritic agents and endothelial cell growth promoters, such as a vascular endothelial growth factor (VEGF) or a polypeptide functional analog, while the relatively slow-eluting microfibers contain at least one bioactive agent selected from anti-proliferative agents, antineoplastic agents, antimicrobial agents, and smooth muscle cell growth inhibitors.

From a technological perspective, the present invention is directed to a micromantled, drug-eluting endovascular stent having a high modulus, expandable, porous scaffold onto which is electrostatically spun a stretchable, compliant, microfibrous, non-woven mantle having at least one type of bioactive agent. The processing of the microfibrous mantle involves the steps of (1) dissolving at least one polymer in at least one organic liquid which is at least one solvent to produce at least one uniform solution; (2) dissolving or dispersing at least one bioactive agent in each polymer solution; (3) transferring the product of step 2 to a syringe component of an electrospinning apparatus; and (4) allowing the electrostatically spun microfiber to collect on a metallic stent placed on a grounded, solid holding mandrill which is preferably attached to a larger mandrill for concerted coaxial radial rotation. The holding mandrill may be a non-conductive polymeric rod, grounded through a partially embedded T-shaped metallic strip. Alternatively the rod may have a conducting polymer surface layer formed by polymerizing pyrrole on a selectively treated area of the mandrill surface, the selectively treat area having covalently bound acid functionalities selected from carboxylic acid, sulfonic acid and phosphonic acid.

DETAILED DESCRIPTION OF PREFERRED EMBODIMENTS

Taking into account the stent technology of the prior art and its continued, but less than optimal, evolution toward eliminating the incidence of restenosis following angioplasty, the conceptual framework of this invention was developed using unique approaches to enhanced stent improvement. While the collective changes applied in the prior art towards improving the stent performance did not lead to an ideal, or close to ideal, stent, there have been several independent improvements with each change, which have not been properly integrated to secure a significant overall net improvement. Accordingly, carefully selected and properly synchronized changes in the stent technology to achieve unexpected improvements became the basic tenet of the present invention. A major aspect of the present invention is the novel use of a compliant, soft, microfibrous mantle on the outer surface of a stent to dampen the mechanical stresses exerted by the high modulus primary stent construct against the blood vessel endothelial lining. Equally important is the design of such microfibers and resulting microfabric, wherein the compliance of the mantle is not only characteristic of the total construct by virtue of comprising non-woven, randomly entangled microfiber, but also inherent in the individual microfibers due to the fact that they are made of inherently low modulus (high compliance) polymers, which are electrospun into exceptionally low diameter microfibers having low engineering modulus (high engineering compliance). The physicomechanical and morphological features of the electrospun mantle of the present invention represent a considerable improvement over the tubular solution-cast or fiber-reinforced composite tube disclosed in U.S. Pat. No. 6,797,485 as discussed in the background section and further analyzed below.

Specifically, U.S. Pat. No. 6,797,485 describes a one-phase tubular or composite tubular cover for a stent, wherein the latter comprises a polymeric matrix reinforced with monofilament cross-spiral, wherein at least one of the matrix and reinforcement comprise an absorbable crystalline, monocentric, polyaxial copolyester and wherein the composite tubular cover or mantle can be microporous. However, both the tubular mantle and composite tubular mantle (1) are made independent of the stent and then placed in the stent—this does not provide the exceptional intimacy and surface integration of the mantle electrospun directly onto the stent as described in the present invention; (2) are produced, in part, by casting a polymer solution on the mandrill (not the stent) and then allowed to dry—this does not provide the exceptional uniformity and high surface area characteristic of the electrospun microfibrous mantle subject of the present invention; (3) are made to have much higher bulk density as compared to the electrospun mantle subject of this invention, which provides considerably higher compressibility and engineering compliance—this makes the electrospun mantle a more effective shock absorber between the high modulus metallic stent and the soft luminal wall, as compared to the mantle of U.S. Pat. No. 6,797,485 with its relatively high bulk density; and (4) have a much lower surface/volume ratio and practically one type of matrix that provides one diffusion pathway for drug elution as compared to the electrospun mantle of the present invention, which provides more than one type of matrices with high surface/volume ratio which makes it more suitable for more uniform and precise control of more than one drug at more than one diffusion rate and pathway. Surprisingly, the direct, high pressure contact of the high modulus, metallic, drug-eluting stent struts and the lumen of the arteries are not well documented in the biomedical literature. This is in spite of the fact that such mechanical stresses are a major cause of chronic injuries in the vascular wall, which have been medicated to a limited extent by incorporating immunosuppressant drugs in the stent polymeric coating. One may argue that the polymeric coating prevents the direct physical contact of the metallic surface with the vessel lining. However, the damaging contact is primarily mechanical and not a mere physical one. The low modulus polymeric thin coating would hardly affect the load transfer from the metallic construct to the lining, hence, no reduction in the stress concentration at the interface would be expected.

Another unresolved problem associated with the present art of the drug-eluting stent is the use of pharmaceutical compounds that beneficially inhibit the growth proliferation of the smooth muscle cells, but may adversely inhibit the desirable growth of endothelial cells, which are needed to cover the compromised part of the lumen of the treated vessel in a timely manner. Accordingly, this invention deals with a microporous stent mantle that (1) plays the role of shock absorber between the metallic construct and vessel lining; (2) functions as a high surface area matrix with modulated morphology to provide a timely and precise release of at least one bioactive agent in a timely manner; and (3) can be used to incorporate more than one drug in separate microfibers, which, in turn, allows the use of a first drug that specifically inhibits the growth and proliferation of the smooth muscle, and a second one which is designed to promote the endothelial growth without contending with drug-drug interaction as would be the case when a stent coating is used as drug-containing matrices of both drugs.

In meeting the challenge of producing a compliant, stretchable microfibrous mantle, this invention addresses the need for high molecular weight polymeric materials which (1) are inherently complaint; (2) can easily be converted to electrospinnable solutions based on solvents that do not alter the chemical structure of the bioactive agents during the electrospinning process; and (3) do not alter the chemistry of the bioactive agents during the electrospinning process. Among the typical examples of polymers that are useful for the production of electrospun microfibrous mantles, subject of this invention, are (1) the absorbable, compliant, crystalline copolymers described in U.S. Pat. No. 6,462,169 (2002) and U.S. Pat. No. 6,794,485 (2004); (2) absorbable caprolactone polymers of U.S. Pat. No. 6,197,320 (2001); (3) the bioswellable, crystalline, amphiphilic block/graft polymers of U.S. Patent Application Ser. No. 60/690,751 (Jun. 15, 2005) based on polyethylene glycol copolyester with cyclic lactones and carbonates; (4) the crystalline, high compliance glycolide copolymers based on segmented copolymers of lactide and other cyclic monomers of U.S. patent application Ser. No. 10/767,975 (Jan. 29, 2004); (5) compliant, longlasting, absorbable polymer of PCT Application Serial No. 05/42978 (Nov. 29, 2005); (6) functionalized, absorbable, segmented copolyesters of U.S. patent application Ser. No. 10/693,361 (Oct. 24, 2003); and (7) the amphiphilic methacrylate copolymers described in PCT Application Serial No. 05/24120 (Jul. 8, 2005).

To produce a micromantled metallic stent comprising a microfibrous, non-woven mantle formed directly onto the metallic stent, this invention deals with a new electrospinning process. This is a modification of the method disclosed in U.S. patent application Ser. No. 11/175,635 (Jul. 5, 2005), wherein the receiving metallic drum is replaced by a polymeric mandrill serving as a holder of the metallic stent and, in effect, as the receiving electrode. To ground the metallic stent, a partially embedded T-shaped, conductive metallic wire (or narrow film) comprising a radial conductive band (or strip), continued axially toward the end of the mandrill as a linear conductive strip, is used to allow the electric current to flow from the stent to the grounding point. Alternatively, the T-shaped conducting components are formed through the steps of (1) selective surface activation of the intended area of the mandrill surface to introduce covalent bonded carboxylic, sulfonic, or phosphonic groups following the teaching of U.S. Pat. No. 5,849,415 (1998) and U.S. Patent Application Ser. No. 60/662,908 (Mar. 17, 2005); and (2) directed surface polymerization of pyrrole to form the conductive T-shaped film, following the teaching of U.S. Pat. No. 5,849,415 (1998) and U.S. Patent Application Ser. No. 60/662,908 (Mar. 17, 2005). Among the non-conductive polymers which can be used to produce mandrills are high density polyethylene, ultrahigh molecular weight polyethylene, nylon 12, and polyether-ether ketone.

To satisfy the clinical needs which have not been met in disclosures of the prior art on drug-eluting stents, in terms of providing the effective concentration of bioactive active agents in a timely manner, the present invention provides for the use of a series of agents which can be highly efficacious in controlling virtually all the biological events leading to restenosis. Among the typical examples of these agents that can be used individually or in different combinations in separate microfibers are those discussed below:

(1) Paclitaxel, is an antineoplastic compound which is used clinically in commercially available drug-eluting stents. This drug can also be used as an anti-inflammatory agent with an exceptionally narrow therapeutic window beyond which it can be cytotoxic. Accordingly, this invention provides for the use of paclitaxel in different fractions of the microfibers in the capacity of an antineoplastic agent in combination with other drugs known for their anti-inflammatory activities (e.g., naproxen) and/or being immunosuppressant (e.g., rapamycin).

(2) Rapamycin is clinically used in commercially available drug-eluting stents. This drug is also used as an immunosuppressant having a wide therapeutic window. However, its use in drug-eluting stents in the prior art may not provide the optimum pharmacokinetics when released from a non-uniform coating. Accordingly, the present invention provides for the use of rapamycin at two drug loadings in different fractions of the microfibrous mass of the stent mantle—one set of microfibers provides an initial burst and the second set of microfibers provides a prolonged, sustained release of the drug at lower concentrations. This invention also provides for use of rapamycin in combination with at least one additional bioactive agent, with different pharmacological activity in one or more set of microfibers of the mantle's microfibrous mass. Typical examples of these other agents include endothelial cell growth promoters (e.g., vascular endothelial growth factor or its polypeptide functional analog), smooth muscle growth inhibitors, and antibiotics.

(3) Antineoplastic agents, such as dactimycin, doxorubicin, mitomycin, mitoxantrone, and topotecan, which also exhibit antibiotic activities. These can be used individually or in combination with other drugs (loaded in separate microfibers), particularly those known to exhibit anti-inflammatory activity and/or promote endothelial cell growth.

(4) Antineoplastic agents are also folate antagonists, such as methotrexate. The latter drug is also antimetabolite and immunosuppressant but can be an irritant. To mediate the latter effect, methotrexate can be used in combination with an anti-inflammatory drug and/or endothelial cell growth promoters, such as vascular endothelial growth factor (VEGF) or its polypeptide functional analog (loaded in different microfibers).

(5) Anti-inflammatory drugs, which can be used alone or in combination with antineoplastic agents and/or immunosuppressants (loaded in different microfibers). Examples of these anti-inflammatory drugs include (a) colchicine, which is also an antineoplastic compound that can be used to retard smooth muscle cell proliferation and can preferably be used in combination with an endothelial cell growth promoter, such as VEGF or its polypeptide functional analog; (b) the NSAID, indomethacin; (c) the NSAID, piroxicam, which may also be an immunosuppressant; and (d) the corticosteroid, prednisone, which may also exhibit antineoplastic activity.

(6) Leflunamide, a member of the isoxazole class of drugs, exhibits anti-inflammatory, antiproliferative, and immunosuppressive activities. This can be used alone or in combination with an endothelial cell promoter.

(7) Thalidomide is an anti-inflammatory drug that also exhibits anti-angiogenic and immunosuppressive activities. This can be used alone or in combination with an endothelial cell growth promoter.

(8) Curcumin is an anti-inflammatory drug, which also exhibits antiproliferative activities.

(9) Mycophenolate mofetil is an immunosuppressant that is endowed with anti-inflammatory properties. This can be used alone or in combination with an endothelial cell promoter (loaded in different microfibers).

(10) Methotrexate is an anti-inflammatory and immunoregulatory drug. It exhibits antiproliferative activity and can be used alone or in combination with an endothelial cell growth promoter, such as vascular endothelial growth factor or its polypeptide functional analog (loaded in different microfibers).

(11) Dihydrofolate reductase is an anti-infective, antineoplastic, and anti-inflammatory agent. It can be used alone or in combination with an endothelial cell growth promoter.

(12) Deferoxamine has been used extensively as chelation therapy in iron-loaded states and noted recently for its usefulness as an antiproliferative, anti-inflammatory, and immunosuppressive agent (Weinberg, K., *Am. J. Pediatr. Hematol. Oncol.* 12, 9, 1990). It can be used alone or in combination with an endothelial cell growth promoter (loaded in different microfibers).

(13) Antibiotics produced by members of the bacterial genus *Streptomyces*, such as streptomycin-B, actinomycin-F1, and actinomycin-D, also exhibit antineoplastic and/or immunosuppressive activities.

(14) Antineoplastics which are also antimetabolites, such as fludarabine and fluorouracil, can be used alone or in combination with an anti-inflammatory drug.

In concert with one of the basic tenets of this invention dealing with use of drug combinations, a key aspect of the present invention is the electrostatic spinning of drug-loaded polymeric solutions under special conditions to load the different drugs individually and in separate microfibers. Accordingly, a specific aspect of this invention deals with an electrospinning system comprising more than one syringe, each prepared to dispense one particular drug. The solutions used in all the syringes may or may not comprise the same polymer. The delivery (or extrusion) of the drug-loaded polymer solution from the different syringes can be executed in series, simultaneously or intermittently through a concerted order of series and parallel modes of delivery.

Further illustrations of the present invention are provided by the following examples:

EXAMPLE 1

Synthesis and Characterization of Typical Absorbable, Compliant, Polyaxial, Segmented Copolyesters (Co-P1)

Following a similar method to that described in U.S. Pat. No. 6,462,169, a triaxial polymeric copolymer was made from 50/50 (molar) caprolactone and trimethylene carbonate (TMC) and then end-grafted with 90/10 (molar) l-lactide/TMC. Accordingly, the polymeric initiator was prepared by ring opening polymerization of ε-caprolactone (0.25 mole) and TMC (0.25 mole) in the presence of stannous octanoate as a catalyst (at a monomer/catalyst ratio of 15,000) and triethanolamine as the initiator (at a monomer to initiator ratio of 300). The polymerization was achieved by heating at 180° C. for 3 hours. The resulting product was cooled below 150° C. and then mixed under nitrogen atmosphere with l-lactide (0.45 mole) and ε-caprolactone (0.05 mole). The system was stirred while heating to 190-200° C. to achieve a uniform melt. The temperature was then lowered to 140° C. and the reaction was continued without stirring for 24 hours. The polymer was isolated, ground, dried, and heated under reduced pressure to remove unreacted monomer. The polymer was characterized by IR and NMR (for identity), GPC ($M_w$=130 kDa), thermal transition ($T_m$=155° C.), and inherent viscosity (I.V.) in chloroform (I.V.=1.0 dL/g).

EXAMPLE 2

Preparation and Characterization of Absorbable, Amphiphilic Polyether-ether Block Copolymer (Co-P2)

This is prepared by first end-grafting polyethylene glycol (molecular weight=20 kDa) (10 g) with trimethylene carbonate (10 g) in the presence of stannous octanoate as a catalyst at monomer/catalyst molar ratio of 6,000 at 165° C. until practically complete monomer conversion is achieved. The product of the reaction is reacted further with a mixture of l-lactide (102 g) and glycolide (8 g) at 165° C. until a practically complete monomer conversion is achieved. The resulting product is isolated and purified by distilling residual monomers by heating at about 90° C. under reduced pressure. The purified polymer is characterized for molecular weight (GPC), thermal transition (DSC), identity (IR), and composition (NMR).

EXAMPLE 3

C-Succinylation of Co-P2 from Example 2 and Characterization of Resulting Acid-bearing Copolymer (Co-P3)

Co-P2 from Example 2 is reacted with maleic anhydride under free-radical conditions to covalently bond the acid-producing functionalities to the copolyether-ester (Co-P2) main chain. In a typical run, this entails heating the polyether-ester (20 g) in dry dioxane (100 mL) with benzoyl peroxide (350 mg) for 4 hours at 85° C. The product is precipitated in ice-water, isolated, and dried under reduced pressure (at 25° C., 40° C., and then 50° C.). The dried product is then characterized for identity (IR and NMR), molecular weight (GPC), and carboxyl content (acidimetry). To convert residual anhydride groups, if any, the resulting product is further hydrolyzed, selectively, (by heating a concentrated dioxane solution at 50° C. for 2-6 hours followed by precipitation and drying) to yield the desired carboxylic acid-bearing C-succinylated liquid polymer (Co-P3). This is then characterized for composition (NMR, IR), carboxyl content (acidimetry), and molecular weight (GPC).

EXAMPLE 4

Preparation and Characterization of Long-lasting 88/14 Segmented l-Lactide/Trimethylene Carbonate Absorbable Copolymer (Co-P4) (PLTMC)

The copolymer (Co-P4) was prepared following the teaching of U.S. Pat. No. 6,342,065 by the two-step copolymerization of l-lactide with trimethylene carbonate in the presence of 1,3-propanediol and stannous octanoate as the initiator and catalyst, respectively. The polymer was isolated, ground, dried, and heated above 80° C. under reduced pressure to remove residual monomer. The polymer was characterized for identity (IR), thermal properties (DSC), and molecular weight by GPC($CH_2Cl_2$). The polymer was shown to have a $T_m$=166° C. and $M_w$=160 kDa. The copolymer was then compression molded into a 0.1 mm-thick film at 180° C.

EXAMPLE 5

Preparation of C-succinylated Derivative (Co-P5) of PLTMC from Example 4

The polymer from Example 4 (CoP4) is reacted with maleic anhydride under free-radical conditions similar to those used in Example 3. Isolation and characterization of C-succinylated PLTMC are conducted as noted for the polymers of Example 3.

EXAMPLE 6

Synthesis and Characterization of Non-absorbable, Amphiphilic, Segmented, Alkyl Methacrylate Copolymer General Method The copolymerization is carried out in two steps. In the first step, N-vinyl pyrrolidone or methacrylic acid, a small amount of one or more alkyl methacrylate(s), and a catalytic amount of a free-radical initiator is mixed under an oxygen-free environment in a mechanically stirred reaction flask. The mixture is heated for about 30 minutes at 65° C.-85° C. to allow partial polymerization of the comonomers. At this point, the second step commences by adding a solution of alkyl methacrylate and an additional amount of the free-radical initiator over a long period of time. After completing the addition of the second charge, the reaction is continued for an additional 30 minutes. When the copolymer formation essentially has ceased, as determined by gel permeation chromatographic analysis of unreacted comonomer, the reaction is terminated and the copolymer is precipitated in water, rinsed with dry ice-cooled methanol. Further purification of the copolymer is accomplished by precipitating its chloroform solution into dry ice-cooled methanol. The purified product is then filtered and dried at room temperature in a laminar flow hood and then at 40° C. under reduced pressure until a constant weight is attained.

The purified copolymer is characterized for molecular weight (GPC), identify (IR), and composition (NMR and elemental nitrogen analysis).

EXAMPLE 7

Synthesis and Characterization of Segmented 20/40/40 (Molar) N-Vinyl Pyrrolidone (VP), n-Butyl Methacrylate (BMA), n-Hexyl Methacrylate (HMP) Copolymer (Co-P6)

The preparation of Co-P6, its isolation, purification, and characterization are conducted following the general method described in Example 6. More specific details are provided below.

The first charge is made of a n N-vinyl-2-pyrrolidone (NVP) rich comonomer mixture. Thus NVP (0.20 mole), n-butyl methacrylate (BMA) (0.05 mole), n-hexyl methacrylate (HMA) (0.05 mole), 1,4-dioxane (49 mL) and 2-2' Azo-bis-isobutyronitrile (2.4 mmole) are mixed/dissolved. The mixture is sparged with nitrogen for two minutes, added to a flask that is kept under a positive nitrogen pressure, and mechanically stirred at 60 RPM in a 65° C. silicon oil bath for a total of 30 minutes. For the second charge, HMA (0.35 mole), BMA (0.35 mole), 1,4-dioxane (49 mL), and 2-2' Azo-bis-isobutyronitrile (2.31 mmole) are mixed/dissolved. The mixture is sparged with nitrogen for 2 minutes and added to the product of the first charge at a constant flow rate (controlled by a peristaltic pump) over a period of 18 hours. The reaction is allowed to continue at 65° C. for an additional 30 minutes.

The polymer is precipitated in ice water in a blender, filtered using a filter funnel, blended in −60° C. methanol, filtered and dried under reduced pressure at room temperature. It is dissolved as a 20-weight-percent solution in chloroform, precipitated in −60° C. methanol, filtered, dissolved in chloroform, poured onto a Teflon tray, and dried to constant weight under reduced pressure at 45° C. Co-P6 is characterized for molecular weight (GPC), identity (IR), and composition (NMR and elemental nitrogen analysis).

EXAMPLE 8

Production of a Typical Microfibrous Mantle on Stainless Steel Stent Using a Modified Electrospinning Method Using standard equipment for electrostatic spinning, at least one solution of at least one polymer in at least one solvent (e.g., chloroform, $CHCl_3$ and/or dichloromethane DCM, acetone or a mixture of acetone and methanol and a mixture of acetone and water) is electrospun using (1) 10 to 35 percent (w/v) solution containing a known amount of a soluble drug or a dispersion of drug micro-/nanoparticles, depending on the molecular weight of the polymer or polymers; (2) a voltage differential of 15-20 KV depending on the sought fiber diameter; (3) a tip-to-collection distance (distance between extruder and collection unit) of 7-10″ depending on the desired diameter and solvent used; and (4) a solution (or dispersion) delivery rate of 0.05 to 0.3 mL/min. depending on the solvent volatility. In most cases, heating of the surrounding environment may not be required. The resulting microfibers are collected on a metallic microporous stent held on a metallic stainless steel, axially micro-grooved holder (having an outside diameter to fit intimately to the inside diameter of the stent), coaxially attached to a grounded, rotating mandrill, capable of controllable radial and axial motion. The electrospun microfiber diameter can be modulated by controlling the polymer concentration and voltage. The thickness of the microporous mantle formed on the stent can be varied by controlling the electrospinning rate and time. The mantled stents are removed and dried prior to packaging.

EXAMPLE 9

Characterization and Testing of the Polymeric Mantle and Mantled Stent

A few mantles are used for subsequent characterization for (1) bulk composition using NMR and IR; (2) surface composition using electron spectroscopy for chemical analysis (ESCA); (3) microfiber diameter and microfabric thickness/uniformity (SEM); (4) molecular weight (GPC, inherent viscosity); and (5) thermal transitions associated with crystalline melting, glass transition melting, or heat of fusion (DSC). A set of mantled stents is used for radial deformation under simulated in vivo deployment and inflation using a typical angioplasty balloon system. A second set of inflated (1.5-2.5×) mantled stents is used to (1) determine surface energy using dynamic contact angle measurement; (2) determine the effect of aging in a phosphate buffered solution at pH 7.4 and 37° C. for 1, 2, 7, 14, 21, 28, and 35 days on microfiber morphology and mantle mass loss; and (3) release rate of active ingredient(s).

Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that aspects of the various embodiments may be interchanged in whole or in part. Therefore, the spirit and scope of the appended claims should not be limited to descriptions and examples herein.

What is claimed is:

1. A process for preparing a micromantled, drug-eluting endovascular stent, the stent comprising a scaffold and a stretchable, compliant microfibrous, non-woven mantle directly on the scaffold, comprising the steps of
   (1) dissolving at least polymer in at least one organic liquid comprising at least solvent to produce at least one uniform solution;
   (2) dissolving or dispersing at least one bioactive agent in each polymer solution;
   (3) transferring the product of step 2 to a syringe component of an electrospinning apparatus; and
   (4) electrostatically spinning at least one type of microfiber directly onto a metallic stent placed on a grounded, solid holding mandrill, wherein the grounded, solid holding mandrill is attached to a larger mandrill for concerted coaxial radial rotation and wherein the holding mandrill comprises a non-conductive polymeric rod, grounded through a partially embedded T-shaped metallic strip.

2. The process set forth in claim 1 wherein the holding mandrill comprises a non-conductive polymeric rod having a surface layer comprising a conducting polymer, formed by polymerizing pyrrole onto a selectively treated area of the rod surface, the selectively treated area having covalently bound acid functionalities selected from the group consisting of carboxylic acid, sulfonic acid, and phosphoric acid.

* * * * *